United States Patent
Commereuc et al.

(10) Patent No.: US 6,646,173 B2
(45) Date of Patent: Nov. 11, 2003

(54) SEQUENCE OF PROCESSES FOR OLEFIN OLIGOMERISATION

(75) Inventors: Dominique Commereuc, Meudon (FR); Alain Forestiere, Vernaison (FR); François Hugues, Vernaizon (FR); Hélène Olivier-Bourbigou, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 186 days.

(21) Appl. No.: 09/984,053

(22) Filed: Oct. 26, 2001

(65) Prior Publication Data

US 2002/0052537 A1 May 2, 2002

(30) Foreign Application Priority Data

Oct. 27, 2000 (FR) .............................................. 0013889

(51) Int. Cl.[7] .............................. C07C 2/02; C07C 2/06; C07C 2/26
(52) U.S. Cl. ...................... 585/517; 585/523; 585/527; 585/531
(58) Field of Search ................................. 585/517, 523, 585/527, 531

(56) References Cited

U.S. PATENT DOCUMENTS 6,444,866 B1 * 9/2002 Commereuc et al. ....... 585/517

FOREIGN PATENT DOCUMENTS

FR          2 765 573 A1      1/1999

* cited by examiner

*Primary Examiner*—Walter D. Griffin
*Assistant Examiner*—Tam M. Nguyen
(74) *Attorney, Agent, or Firm*—Millen, White, Zelano & Branigan, P.C.

(57) ABSTRACT

A process is described for carrying out olefin oligomerisation in two catalysis steps of different types, using an organic feed containing at least one olefin. The cut to be treated, containing at least one olefin ($C_n$), is introduced into a first reaction zone where, in a first step, it undergoes catalytic oligomerisation either of the homogeneous liquid phase type, or of the heterogeneous type with a solid support. The effluent produced is generally sent to a heat exchanger traversed by a cold liquid, the effluent thus being cooled before being sent to a second reaction zone where it undergoes catalytic oligomerisation in a liquid—liquid two-phase medium, the invention being characterized in that at least an ethylenic hydrocarbon containing 3 to 5 carbon atoms per molecule is added to the inlet to the second reaction zone.

20 Claims, No Drawings

SEQUENCE OF PROCESSES FOR OLEFIN OLIGOMERISATION

The present invention relates to an improvement in a dimersol—difasol plant as described in French patent application FR-B-2 765 573, hereby incorporated by reference, which contains practical details regarding carrying out the process.

In this case, the dimersol is the first step; the difasol process is the second step.

The olefin transformation field has been studied in depth and has formed the subject matter of many patents. Particularly advantageous processes are those that can produce long chain oligomers. Depending on the number of carbon atoms in the chain, such oligomers have applications in chemistry, in petrochemistry, or they form part of the composition of gasoline. In the present invention, depending on the case, the reactions of interest will be olefin dimerisations, co-dimerisations or oligomerisations.

The present invention employs a sequence of processes to carry out, in two steps, olefin dimerisation, co-dimerisation or oligomerisation; in the remainder of this text, the term "oligomerisation" will cover these three types of reactions.

The first catalytic oligomerisation step of the process of the invention is homogeneous liquid phase catalysis, or heterogeneous catalysis using a solid catalyst. The type of catalyst and the catalyst are selected as a function of the olefin or olefins to be treated and of the product or products to be obtained in the majority. In the case of homogeneous liquid phase catalysis, the catalytic composition is as follows: the catalyst is a nickel compound or a mixture of nickel compounds, the co-catalyst is an alkyl aluminium compound or a mixture of alkyl aluminium compounds or an aluminium halogenoalkyl compound or a mixture of aluminium halogenoalkyl compounds or a halogenoacetic acid or a mixture of halogenoacetic acids and the optional additive to the catalyst can be a compound with an acidic nature, the anion corresponding to this acid, a carboxylic acid ester, an epoxy compound or a phosphine. The catalysts, co-catalysts and optional additives are introduced into a reactor with an internal temperature of about −40° C. to +100° C., the pressure is such that the reactants are at least partially, preferably mainly in the liquid phase, and the stirring conditions are the conditions necessary to convert at least a portion of the feed. Energetic mechanical stirring is applied to obtain a maximum degree of conversion to oligomers. After this first reaction step, it is optionally possible to isolate the oligomers obtained and/or inhibit the catalyst and/or wash the effluent.

The second step of the process of the invention, the "difasol" process, is an oligomerisation in a liquid—liquid two-phase medium. The reaction medium is a medium with an ionic nature that is not, or is only slightly, miscible with the organic phase containing at least one catalyst that is a nickel complex or a mixture of nickel complexes and possibly at least one additive to the catalyst. The polar phase can also be an ionic medium that is not miscible with the organic phase containing no catalyst, the catalyst for the liquid—liquid two-phase medium oligomerisation reaction is then the catalyst used in the first step (in this case, the first step is a homogeneous catalyst). The catalyst is then introduced into the reactor with the effluent leaving the reactor from the first step.

The medium with the ionic nature comprises at least one salt with formula $Q^+A^-$, in which $Q^+$ is a quaternary ammonium or phosphonium cation or a mixture of the two, or a lithium cation, and $A^-$ is a co-ordinating or non co-ordinating anion selected from the group formed by halogenoaluminates, organohalogenoaluminates, organogallates, organohalogenogallates or a mixture of at least two of such compounds.

For this second step, after injecting the feed to be treated, a two-phase medium is obtained which has to be stirred vigorously to ensure good contact between the two phases, this contact being necessary to obtain a good range of conversion into oligomers. In one implementation that can produce good yields, stirring is partially provided by recycling a mixture of the two reaction liquids: the emulsion contained in the reactor is continuously withdrawn and decanted. After decanting, two phases are obtained: an organic supernatant phase is isolated then cooled using a heat exchanger. This cooling can keep the temperature inside the reactor constant and can prevent the catalyst from being damaged by continuous monitoring. A quantity of fresh polar phase, equal to the quantity of polar phase withdrawn and decanted, is injected into the reactor.

After catalysis, for example liquid—liquid two phase catalysis, the effluent from the reactor outlet is washed using a basic solution then water, the oligomers obtained are isolated. This wash can optionally be common with washing of the oligomers produced during the first step, if the latter is carried out.

The cut to be treated containing at least one olefin ($C_n$) is introduced into a reaction zone where in a first step it undergoes catalytic oligomerisation, either of the homogeneous type carried out in the liquid phase, or of the heterogeneous type carried out with a solid support. The effluent produced is sent to a heat exchanger traversed by a cold liquid. The effluent is thus cooled before being sent to a second reaction zone where it undergoes catalytic oligomerisation in a liquid—liquid two-phase medium. The invention is characterized in that at the inlet to this second reaction zone, at least one $C_3$, $C_4$ or $C_5$, ethylenic hydrocarbon is added. After the reaction, the effluent is directed to a washing zone. After washing, the hydrocarbon fraction is sent to a separator. The fraction containing unreacted olefins ($C_n$) is separated from the fraction of oligomers produced, this fraction $C_n$ is evacuated from the apparatus. If a mixture of oligomers is obtained after the reaction, this latter fraction is sent to a zone in which it undergoes a second separation step to isolate the desired products from the $C(2_{n+1})+$ mixture.

It is also possible to envisage, at the outlet from the second reaction zone, the separation string "$NH_3+NaCH+H_2O$" before final separation of the desired products from the unconverted products.

In summary, the invention concerns a process for carrying out a dimerisation, co-dirnerisation or oligomerisation reaction on an organic feed containing at least one olefin, characterized in that it comprises at least two successive catalysis steps of different types.

The second step is oligomerisation in the presence of at least one catalytic element in a liquid—liquid two-phase medium containing a medium with an ionic nature that is not or is only slightly miscible with the organic phase, containing at least one olefin the chain of which contains two to six carbon atoms or a mixture of said olefins, the process being characterized in that at least one $C_3$, $C_4$ or $C_5$ olefin is added to the inlet to the second reaction zone.

Preferably, at least a portion of the feed that has not reacted during the first step is introduced, optionally after a catalyst inhibition treatment, into a two-phase medium in which the temperature is about −50° C. to +100° C. and the pressure is about 0.01 to 20 MPa, stirring being provided at least in part by circulating a mixture of the two reaction liquids in a closed loop, and after reaction, the effluent is decanted.

Preferably again, the catalyst used for two-phase oligomerisation is a nickel complex or a mixture of nickel complexes and the medium with the ionic nature comprises at least one salt with formula $Q^+A^-$, in which $Q^+$ is a quaternary ammonium or phosphonium cation or a mixture of the two or a lithium cation, and $A^-$ is a co-ordinating or non co-ordinating anion.

Generally, after undergoing an oligomerisation reaction in a two-phase medium then decanting the mixture of reaction liquids, the effluent is washed then the oligomers produced are separated from the unreacted hydrocarbons.

The effluent obtained after the first catalysis step is washed, the oligomers produced are isolated, and the compounds that have not reacted during this first step are dried before undergoing said oligomerisation in a liquid—liquid two-phase medium in the second step.

Preferably again, the first step and the oligomerisation in a two-phase medium are followed by washes, the wash subsequent to the first step being carried out in the same zone as the wash following oligomerisation in a two-phase medium.

The first step is advantageously carried out by homogeneous catalysis in the liquid phase; in the first step, the catalyst is a nickel compound or a mixture of nickel compounds, the co-catalyst is an alkyl aluminium compound or a mixture of alkyl aluminium compounds or a halogenoalkyl aluminium compound or a mixture of halogenoalky aluminium compounds.

Advantageously again, in the first step, the olefin or olefins to be treated are introduced continuously into a reaction zone that is continuously supplied with catalytic composition at a temperature of about −40° C. to +100° C., at a pressure such that the reactants are at least partially in the liquid phase and under the stirring conditions necessary to obtain a maximum degree of conversion of the feed into dimers, co-dimers, oligomers or at least a mixture of two of these types of compound.

What is claimed is:

1. A process for carrying out a dimerisation, co-dimerisation or oligomerisation reaction on an organic feed containing at least one olefin, comprising at least two successive catalysis steps of different types, the first step comprising contacting the feed under homogeneous or heterogeneous catalysis conditions and the second step comprising oligomerizing at least a portion of the resultant effluent from the first step in the presence of at least one catalytic element in a liquid—liquid two-phase medium containing an organic phase and a medium with an ionic nature that is not or is only slightly miscible with the organic phase, the feed to be treated containing at least one olefin the chain of which contains two to six carbon atoms or a mixture of said olefins, the process being characterized in that at least one olefin selected from the group consisting of $C_3$, $C_4$ and $C_5$ olefins is added at the beginning of the second step.

2. A process according to claim 1, in which at least a portion of the feed that is unreacted during the first step and the unreacted portion is introduced, optionally after a catalyst inhibition treatment, into said two-phase medium in which the temperature is about 50° C. to 100° C. and the pressure is about 0.01 to 20 MPa, stirring being provided at least in part by circulating a mixture of the resultant two reaction liquids in a closed loop, and after reaction, the effluent is decanted.

3. A process according to claim 1, comprising oligomerization in which the catalyst used for two-phase oligomerisation is a nickel complex or a mixture of nickel complexes, and the medium with the ionic nature comprises at least one salt with formula $Q^{+A-}$, in which $Q^+$ is a quaternary ammonium or phosphonium cation or a mixture of the two, or a lithium cation, and $A^-$ is a co-ordinating or non co-ordinating anion.

4. A process for carrying our an oligomerisation reaction on an organic feed according to claim 1, characterized in that the first step is carried out by homogeneous catalysis in the liquid phase, the catalyst being a nickel compound or a mixture of nickel compounds, the co-catalyst being an alkyl aluminium compound or a mixture of alkyl aluminium compounds or a halogenoalkyl aluminium compound or a mixture of halogenoalkyl aluminium compounds.

5. A process according to claim 2, comprising oligomerization in which the catalyst used for two-phase oligomerisation is a nickel complex or a mixture of nickel complexes, and the medium with the ionic nature comprises at least one salt with formula $Q^+A^-$, in which $Q^+$ is a quaternary ammonium or phosphonium cation or a mixture of the two, or a lithium cation, and $A^-$ is a co-ordinating or non co-ordinating anion.

6. A process for carrying out an oligomerisation reaction on an organic feed according to claim 2, characterized in that the first step is carried out by homogeneous catalysis in the liquid phase, the catalyst being a nickel compound or a mixture of nickel compounds, the co-catalyst being an alkyl aluminium compound or a mixture of alkyl aluminium compounds or a halogenoalkyl aluminium compound or a mixture of halogenoalkyl aluminium compounds.

7. A process for carrying out an oligomerisation reaction on an organic feed according to claim 3, characterized in that the first step is carried out by homogeneous catalysis in the liquid phase, the catalyst being a nickel compound or a mixture of nickel compounds, the co-catalyst being an alkyl aluminium compound or a mixture of alkyl aluminium compounds or a halogenoalkyl aluminium compound or a mixture of halogenoalkyl aluminium compounds.

8. A process for carrying out an oligomerisation reaction on an organic feed according to claim 5, characterized in that the first step is carried out by homogeneous catalysis in the liquid phase, the catalyst being a nickel compound or a mixture of nickel compounds, the co-catalyst being an alkyl aluminium compound or a mixture of alkyl aluminium compounds or a halogenoalkyl aluminium compound or a mixture of halogenoalkyl aluminium compounds.

9. A process according to claim 1, wherein said olefins are added continuously at the beginning of the second step.

10. A process according to claim 2, wherein said olefins are added continuously at the beginning of the second step.

11. A process according to claim 3, wherein said olefins are added continuously at the beginning of the second step.

12. A process according to claim 4, wherein said olefins are added continuously at the beginning of the second step.

13. A process according to claim 5, wherein said olefins are added continuously at the beginning of the second step.

14. A process according to claim 6, wherein said olefins are added continuously at the beginning of the second step.

15. A process according to claim 7, wherein said olefins are added continuously at the beginning of the second step.

16. A process according to claim 8, wherein said olefins are added continuously at the beginning of the second step.

17. A process according to claim 1, further comprising separating oligomers from the first step and passing at least a portion of resultant oligomer-depleted effluent to said second step.

18. A process according to claim 2, further comprising said catalyst inhibition treatment of the unreacted portion.

19. A process according to claim 17, further comprising subjecting said oligomer-depleted effluent to a catalyst inhibition treatment prior to passing said oligomer-depleted effluent to said second step.

20. A process according to claim 17, further comprising cooling said at least a portion of die resultant oligomer-depleted effluent prior to passing said effluent to said second step.

* * * * *